US012779173B2

(12) United States Patent
Andersen et al.

(10) Patent No.: US 12,779,173 B2
(45) Date of Patent: Nov. 3, 2026

(54) MULTI-FUNCTION ADAPTER FOR VASCULAR ACCESS DEVICE PLACEMENT

(71) Applicant: Bard Peripheral Vascular, Inc., Franklin Lakes, NJ (US)

(72) Inventors: Christian Andersen, Queen Creek, AZ (US); Diana Fiumefreddo, Salt Lake City, UT (US); Bryon Ray Densley, Rochester, MN (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 275 days.

(21) Appl. No.: 18/701,181

(22) PCT Filed: Oct. 14, 2021

(86) PCT No.: PCT/US2021/055054

§ 371 (c)(1),
(2) Date: Apr. 12, 2024

(87) PCT Pub. No.: WO2023/063956

PCT Pub. Date: Apr. 20, 2023

(65) Prior Publication Data

US 2024/0416077 A1 Dec. 19, 2024

(51) Int. Cl.
*A61B 5/06* (2006.01)
*A61M 25/01* (2006.01)
*A61M 39/10* (2006.01)

(52) U.S. Cl.
CPC ........ *A61M 25/0105* (2013.01); *A61M 39/10* (2013.01); *A61M 2025/0166* (2013.01);
(Continued)

(58) Field of Classification Search
CPC ...................... A61B 5/33; A61B 5/065; A61B 2034/2051; A61B 5/062; A61M 2025/0166; A61M 2039/1022; A61M 2230/06
See application file for complete search history.

(56) References Cited

U.S. PATENT DOCUMENTS 5,269,306 A 12/1993 Warnking et al.
6,063,032 A 5/2000 Grunwald
(Continued)

FOREIGN PATENT DOCUMENTS

DE 4319033 C1 6/1994
WO 2009003138 A1 12/2008
(Continued)

OTHER PUBLICATIONS

PCT/US2021/055054 filed Oct. 14, 2021 International Search Report and Written Opinion dated Jun. 9, 2022.

*Primary Examiner* — Deanna K Hall
(74) *Attorney, Agent, or Firm* — Rutan & Tucker LLP

(57) ABSTRACT

Embodiments disclosed herein are directed to a multi-function adapter system for placing a distal tip of a catheter at a target location. The system is configured to maintain one or more electrical communication pathways with the catheter distal tip during a placement procedure. Two or more electrical pathways can be cross-referenced to determine accuracy. The electrical pathways can include a clip and first tether that provides a versatile electrical pathway in that the clip can be selectively coupled with either a saline column, stylet, guidewire, or needle. A flushing adapter can include a second tether formed integrally therewith and provide a second electrical pathway with a saline column. The stylet or guidewire can be fixedly coupled with the flushing adapter and can provide a second electrical pathway with the second tether. These electrical pathways can provide a fail-safe system to ensure electrical communication with the distal tip of the catheter.

23 Claims, 6 Drawing Sheets

(52) U.S. Cl.
CPC ............... *A61M 2039/1022* (2013.01); *A61M 2039/1077* (2013.01); *A61M 2205/0233* (2013.01); *A61M 2230/06* (2013.01)

(56) References Cited

U.S. PATENT DOCUMENTS

| | | | |
|---|---|---|---|
| 6,102,862 | A | 8/2000 | Grunwald et al. |
| 6,120,445 | A | 9/2000 | Grunwald |
| 6,217,517 | B1 | 4/2001 | Grunwald |
| 6,254,543 | B1 | 7/2001 | Grunwald et al. |
| 6,287,259 | B1 | 9/2001 | Grunwald |
| 6,514,202 | B2 | 2/2003 | Grunwald |
| 6,589,181 | B2 | 7/2003 | Grunwald et al. |
| 6,945,938 | B2 | 9/2005 | Grunwald |
| 7,022,075 | B2 | 4/2006 | Grunwald et al. |
| 8,409,103 | B2 | 4/2013 | Grunwald et al. |
| 8,597,193 | B2 | 12/2013 | Grunwald et al. |
| 9,125,578 | B2 | 9/2015 | Grunwald |
| 9,198,600 | B2 | 12/2015 | Grunwald et al. |
| 9,339,206 | B2 | 5/2016 | Grunwald |
| 9,532,724 | B2 | 1/2017 | Grunwald |
| 9,615,759 | B2 | 4/2017 | Hurezan |
| 9,636,031 | B2 | 5/2017 | Cox |
| 9,901,714 | B2 | 2/2018 | Lemon et al. |
| 10,046,139 | B2 | 8/2018 | Powers et al. |
| 10,231,643 | B2 | 3/2019 | Grunwald |
| 10,271,762 | B2 | 4/2019 | Grunwald |
| 10,349,857 | B2 | 7/2019 | Grunwald |
| 10,912,488 | B2 | 2/2021 | Grunwald |
| 2002/0173721 | A1 | 11/2002 | Grunwald et al. |
| 2003/0013959 | A1 | 1/2003 | Grunwald et al. |
| 2006/0116578 | A1 | 6/2006 | Grunwald et al. |
| 2007/0016069 | A1 | 1/2007 | Grunwald et al. |
| 2007/0016072 | A1 | 1/2007 | Grunwald et al. |
| 2009/0118612 | A1 | 5/2009 | Grunwald et al. |
| 2009/0177090 | A1 | 7/2009 | Grunwald et al. |
| 2010/0318026 | A1 | 12/2010 | Grunwald |
| 2013/0289417 | A1 | 10/2013 | Grunwald et al. |
| 2015/0031987 | A1 | 1/2015 | Pameijer et al. |
| 2015/0289781 | A1 | 10/2015 | Grunwald et al. |
| 2015/0317810 | A1 | 11/2015 | Grunwald et al. |
| 2016/0278869 | A1 | 9/2016 | Grunwald |
| 2018/0070856 | A1 | 3/2018 | Grunwald |
| 2019/0246945 | A1 | 8/2019 | Grunwald |

FOREIGN PATENT DOCUMENTS

| | | | |
|---|---|---|---|
| WO | 2010144922 | A1 | 12/2010 |
| WO | 2011019760 | A2 | 2/2011 |
| WO | 2011097312 | A1 | 8/2011 |
| WO | 2012040487 | A1 | 3/2012 |
| WO | 2023063956 | A1 | 4/2023 |

MULTI-FUNCTION ADAPTER FOR VASCULAR ACCESS DEVICE PLACEMENT

PRIORITY

This application is a U.S. national stage application of International Application No. PCT/US2021/055054, filed Oct. 14, 2021, which is incorporated by reference in its entirety into this application.

SUMMARY

Briefly summarized, embodiments disclosed herein are directed to a multi-function, tip confirmation adapter system for placing a distal tip of a catheter, or similar vascular access device ("VAD") at a target location. Various multi-modal vascular access placement systems can be used to locate, track, and confirm placement of a catheter or similar VAD at a target location within a patient. Placement of the catheter distal tip can be critical for the efficacy of the treatment and to prevent undue trauma to the patient. For example, when placing a catheter within the superior vena cava ("SVC"), if the distal tip of a central venous catheter ("CVC") falls short of the target area, the efficacy of the medication is reduced. If the distal tip is advanced too far, the distal tip can cause arrhythmia. Multi-modal, vascular access device placement systems can use various modalities to image a target area, track the catheter onto the target area, and confirm accuracy of placement of the distal tip of the catheter. Embodiments disclosed herein include a multi-function adapter configured to maintain one or more electrical communication pathways with a distal tip of the catheter during a placement procedure to confirm placement of the distal tip of the catheter.

Disclosed herein is a catheter tip confirmation system including, a catheter adapter having a housing including a first cannula defining a lumen, the first cannula formed of an electrically conductive material, a distal end of the catheter adapter housing configured to engage a proximal end of a catheter and provide fluid communication with the first cannula, a clip coupled to a first tether and engaged with a socket disposed in the catheter adapter housing to releasably engage the first cannula, the clip configured to receive a first ECG signal, a flushing adapter releasably coupled to a proximal end of the catheter adapter housing and configured to provide a saline column within the first cannula and the catheter, the flushing adapter including a second tether fixedly coupled thereto and configured to receive a second ECG signal, and an elongate medical device extending through a lumen of the first cannula, a distal tip of the elongate medical device extending to a distal tip of the catheter, the elongate medical device including a magnet disposed at a distal tip thereof.

In some embodiments, the second tether is coupled to the elongate medical device to receive the second ECG signal from the distal tip of the elongate medical device. In some embodiments, the elongate medical device includes one of a stylet, a guidewire, or a coil-over-core guidewire. In some embodiments, the second tether is coupled to a second cannula defining a lumen of the flushing adapter and in fluid communication with the first cannula, the second tether configured to receive the second ECG signal from the saline column extending to the distal tip of the catheter. In some embodiments, the clip is configured to be selectively detached from the first cannula and coupled with a proximal portion of the elongate medical device to receive the first ECG signal from the distal tip of the elongate medical device.

In some embodiments, the elongate medical device is fixedly coupled to the flushing adapter. In some embodiments, the flushing adapter further includes a flushing arm configured to provide fluid communication therewith. In some embodiments, the flushing adapter further includes a locking valve configured to transition between a locked position and an unlocked position, the locking valve in the locked position configured to inhibit longitudinal movement of the elongate medical device relative to the flushing adapter. In some embodiments, the locking valve further includes a valve member configured to control a fluid flow therethrough in both the locked position and unlocked position.

In some embodiments, the catheter tip confirmation system further includes a console configured to compare one of the first ECG signal and the second ECG signal to determine an accuracy of a location of the distal tip of the catheter. In some embodiments, the console is further configured to detect a magnetic field of the distal tip of the elongate medical device and determine a position of the distal tip of the catheter within the body of the patient. In some embodiments, the first cannula is formed of a metal, alloy, or an electrically conductive material. In some embodiments, the catheter includes one of a central venous catheter, peripherally inserted central catheter, rapidly insertable central catheter, midline catheter, single lumen catheter, multi-lumen catheter, or a dialysis catheter.

Also disclosed is a method of determining a location of a distal tip of a catheter within a body of a patient including, coupling a multi-functional adapter system to a proximal end of the catheter, the multi-functional adapter system including, a catheter adapter including a first cannula formed of a conductive material and in fluid communication with the catheter, a flushing adapter coupled to a proximal end of the catheter adapter, and a clip coupled to a first tether, establishing a saline column within the first cannula and the catheter, extending an elongate medical device through the first cannula and into a lumen of the catheter, receiving a first ECG signal by one of the saline column or the elongate medical device, and receiving a second ECG signal by one of the saline column or the elongate medical device and different from the first ECG signal and determining the location of the distal tip of the catheter using one or both of the first ECG signal and the second ECG signal.

In some embodiments, the method further includes comparing the first ECG signal with the second ECG signal to determine an accuracy of a location of the distal tip of the catheter. In some embodiments, the method further includes engaging the clip with a slot disposed in the catheter adapter housing to contact the first cannula and receive the first ECG signal. In some embodiments, the method further includes engaging the clip with the elongate medical device to receive the first ECG signal. In some embodiments, the flushing adapter includes a second cannula in fluid communication with the first cannula, and a second tether fixedly coupled thereto and configured to receive the second ECG signal.

In some embodiments, the flushing adapter includes a second tether fixedly coupled to the elongate medical device and configured to receive the second ECG signal. In some embodiments, the method further includes detecting a magnetic field strength of a magnet disposed at a distal tip of the elongate medical device to track a location of the distal tip of the catheter within the body of the patient. In some embodiments, the elongate medical device includes one of a stylet, a guidewire, or a coil-over-core guidewire.

In some embodiments, the method further includes disengaging the catheter adapter from the catheter, coupling a subcutaneous access device to the catheter, accessing the subcutaneous access device with an access needle and coupling the clip with the access needle to receive the first ECG signal. In some embodiments, the catheter includes one of a central venous catheter, peripherally inserted central catheter, rapidly insertable central catheter, midline catheter, single lumen catheter, multi-lumen catheter, or a dialysis catheter.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
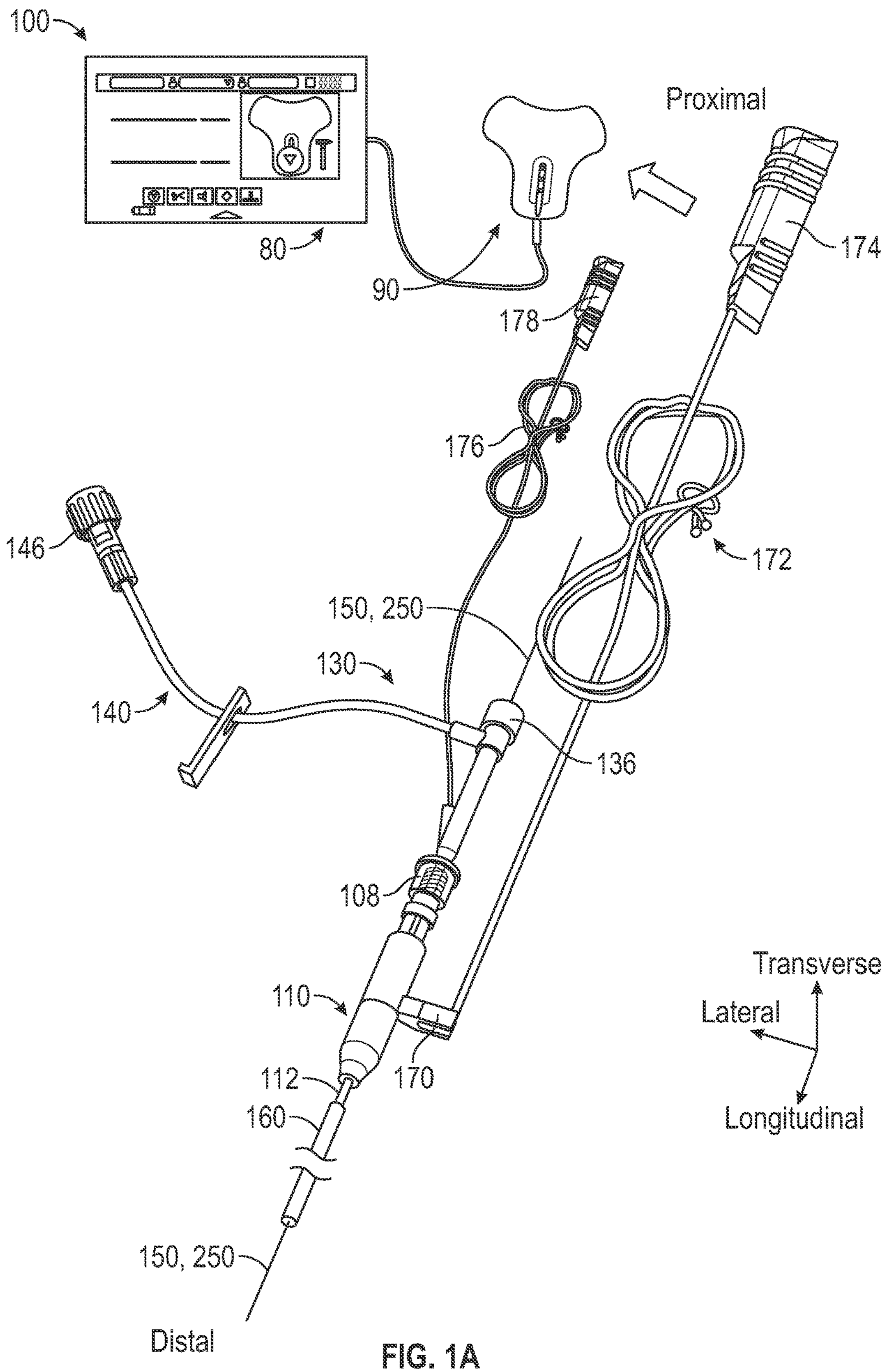
FIG. 1A shows an exemplary multi-function adapter system in an assembled configuration, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive. To assist in the description of embodiments described herein, as shown in FIG. 1A a longitudinal axis extends substantially parallel to an axial length of the catheter. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Figure 1B:
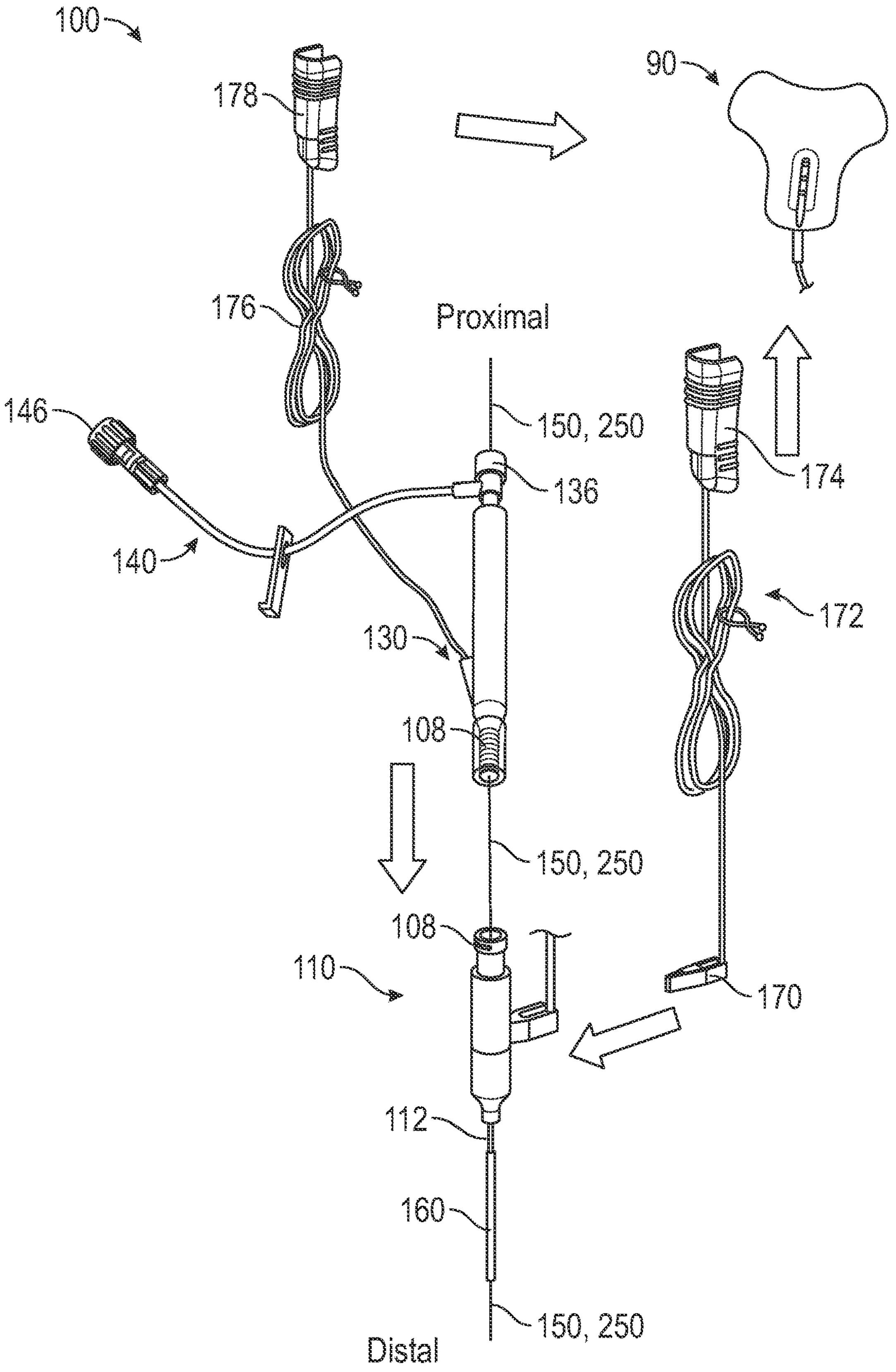
FIG. 1B shows an exploded view of the multi-function adapter system of FIG. 1A, in accordance with embodiments disclosed herein.

FIGS. 1A-1B shows an exemplary multi-function adapter system ("system") 100 for catheter tip confirmation, and generally includes a catheter adapter system ("catheter adapter") 110, a flushing adapter system ("flushing adapter") 130, and an elongate medical device such as a stylet 150 or guidewire 250. FIG. 1A shows the system 100 in an assembled configuration. FIG. 1B shows an exploded view of the system 100 of FIG. 1A. In an embodiment, a distal end of the flushing adapter 130 can be coupled to a proximal end of the catheter adapter 110 and can provide fluid communication therebetween. The flushing adapter 130 can be coupled to the catheter adapter 110 using a connector 108.

Exemplary connectors 108 can include luer lock, twist lock, Tuohy-Borst connectors, or similar suitable medical fluid coupling mechanism. In an embodiment, the connector 108 can include a valve member 106 or similar structure configured to control a fluid flow therethrough in one or both of the connected or unconnected states. In an embodiment, the catheter adapter 110 can be formed integrally with the flushing adapter 130.

In an embodiment, a distal end of the catheter adapter 110 can be coupled with a proximal end of a catheter 160, or similar VAD, and can provide fluid communication therebetween. The catheter adapter 110 can be coupled to the catheter 160 using a luer lock, twist lock, interference fit, press-fit, snap-fit engagement, or similar suitable coupling mechanism. In an embodiment, a cathlock device can further secure the catheter 160 with the catheter adapter 110. As used herein, exemplary catheters 160, or similar VAD's, can include but not limited to central venous catheters (CVC), peripherally inserted central catheters (PICC), rapidly insertable central catheters (RICC), midline catheters, single lumen or multi-lumen catheters, dialysis catheters, or the like. In an embodiment, the stylet 150 can be configured to extend through a lumen of one or more of the catheter adapter 110, flushing adapter 130, and catheter 160, as described in more detail herein.

In an embodiment, the system 100 can further include a clip 170 coupled to a first tether 172 and configured to provide electrical communication therebetween. In an embodiment, the clip 170 can be selectively coupled to one of the catheter adapter 110, flushing adapter 130, stylet 150, or catheter 160. The first tether 172 can be coupled with a multi-modal tracking system 80

, for example, the first tether 172 can include a first fin connector 174 disposed at a proximal end thereof and configured to engage a sensor 90 of a multimodal tracking system 80. As such, the clip 170, first tether 172, and fin connector 174 can be configured to provide an electrical communication pathway between the multi-modal tracking system 80 and one of the catheter adapter 110, flushing adapter 130, stylet 150, or catheter 160, as described herein. As will be appreciated, the fin connector 174 is an exemplary electrical connector and other electrical connector systems are contemplated to fall within the scope of the present invention.

In an embodiment, the flushing adapter 130 can include a second tether 176 formed integrally therewith and configured to provide a second electrical pathway between the flushing adapter 130 and the sensor 90. In an embodiment, the second tether 176 can include a second fin connector 178 disposed at a proximal end thereof and configured to communicatively couple the flushing adapter 130 with the multi-modal tracking system 80, as described herein. In an embodiment, the first tether 172 and the second tether 176 can be coupled to different fin connectors, for example the first fin connector 174 and the second fin connector 178, respectively. In an embodiment, the first tether 172 and the second tether 176 can be coupled to the same fin connector. In an embodiment, one or both of the first tether 172 and the second tether 176 can be coupled directly with a console of the multi-modal tracking system 80.

In an embodiment, the flushing adapter 130 can include a locking valve 136 disposed at a proximal end thereof and configured to selectively control a fluid communication with a lumen of the flushing adapter 130. The locking valve 136 can include a Tuohy-Borst connector, luer lock connector or similar mechanism configured to selectively provide fluid communication with the lumen of the flushing adapter 130. For example, the locking valve 136 can include a collar that can be rotated between a locked and an unlocked position. In the unlocked position, a stylet 150 or guidewire 250 can be advanced through the locking valve 136 and into lumen of the flushing adapter 130. In the locked position, the locking valve 136 can prevent movement of the stylet 150 or guidewire 250 therethrough and either lock the position of the stylet 150 or guidewire 250 relative to the flushing adapter 130, or can prevent the stylet 150 or guidewire 250 from entering the lumen of the flushing adapter 130. In an embodiment, the locking valve 136 can further include a valve member 106, e.g. a bi-leaflet valve, slit valve, duckbill valve, or the like, configured to control a fluid flow through the locking valve 136 in one or both of the locked and the unlocked position. In an embodiment, the flushing adapter 130 can include a flushing arm 140 extending therefrom and in fluid communication with the lumen of the flushing adapter 130. The flushing arm 140 can be coupled with a syringe, medical line, fluid bag, or the like and can provide a fluid to a lumen 102 of the system 100, as described in more detail herein.

FIGS. 2A-2D show cross-section views of embodiments of the system 100. In an embodiment the system 100 can define a lumen 102 extending between a distal end of the catheter adapter 110 and a proximal end of the flushing adapter 130. In an embodiment the catheter adapter 110 can include a first cannula 112 defining a portion of the lumen 102. A distal end of the first cannula 112 can extend distally of the distal end of a housing 114 of the catheter adapter 110 and can be configured to engage a proximal end of the catheter 160 to provide fluid communication with a lumen 162 thereof. In an embodiment, the first cannula 112 can be formed of a metal, alloy, stainless steel, or similar electrically conductive material.

Figure 2A:
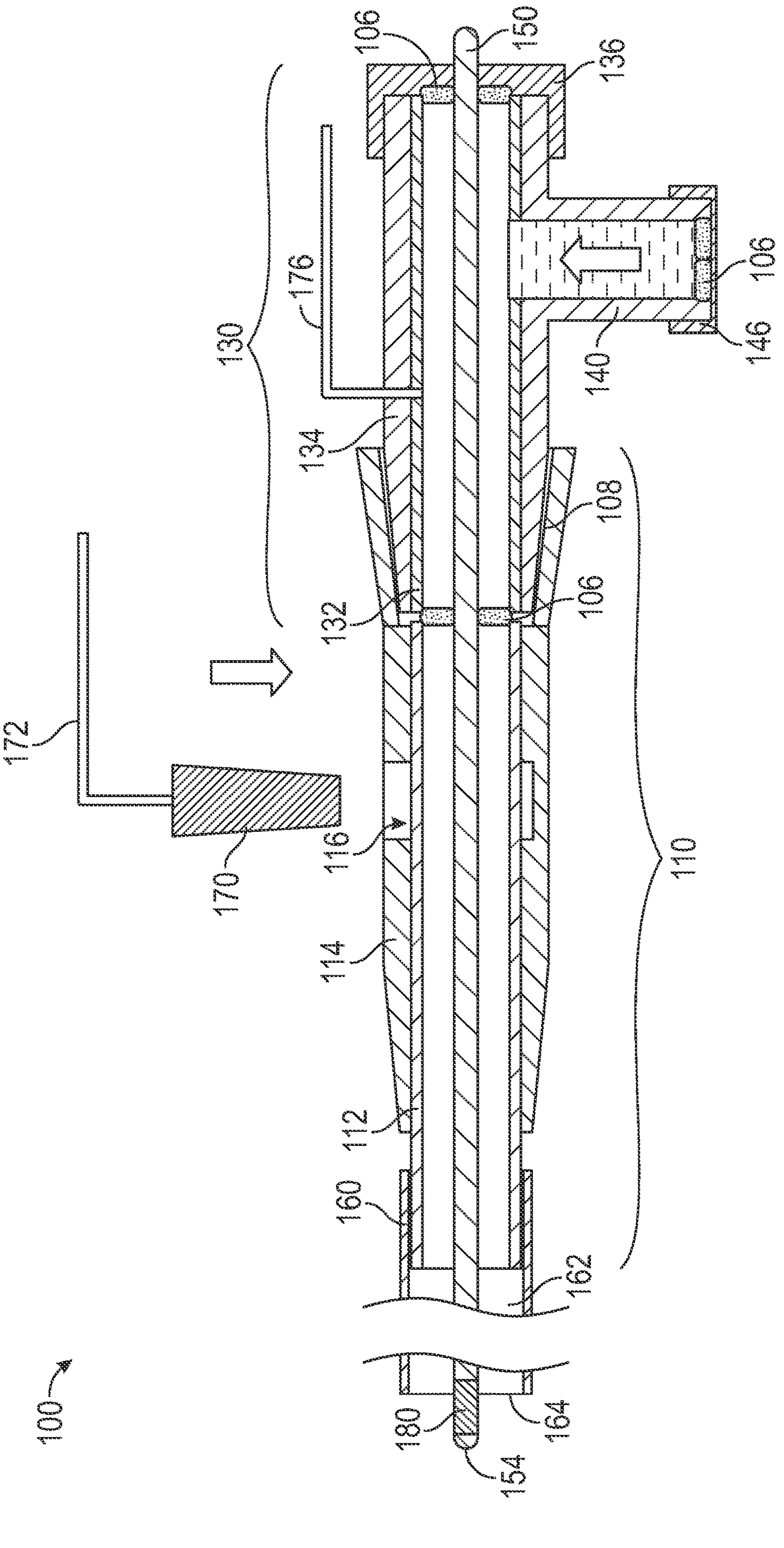
FIG. 2A shows a cross-section view of a multi-function adapter system, in accordance with embodiments disclosed herein.
Figure 2B:
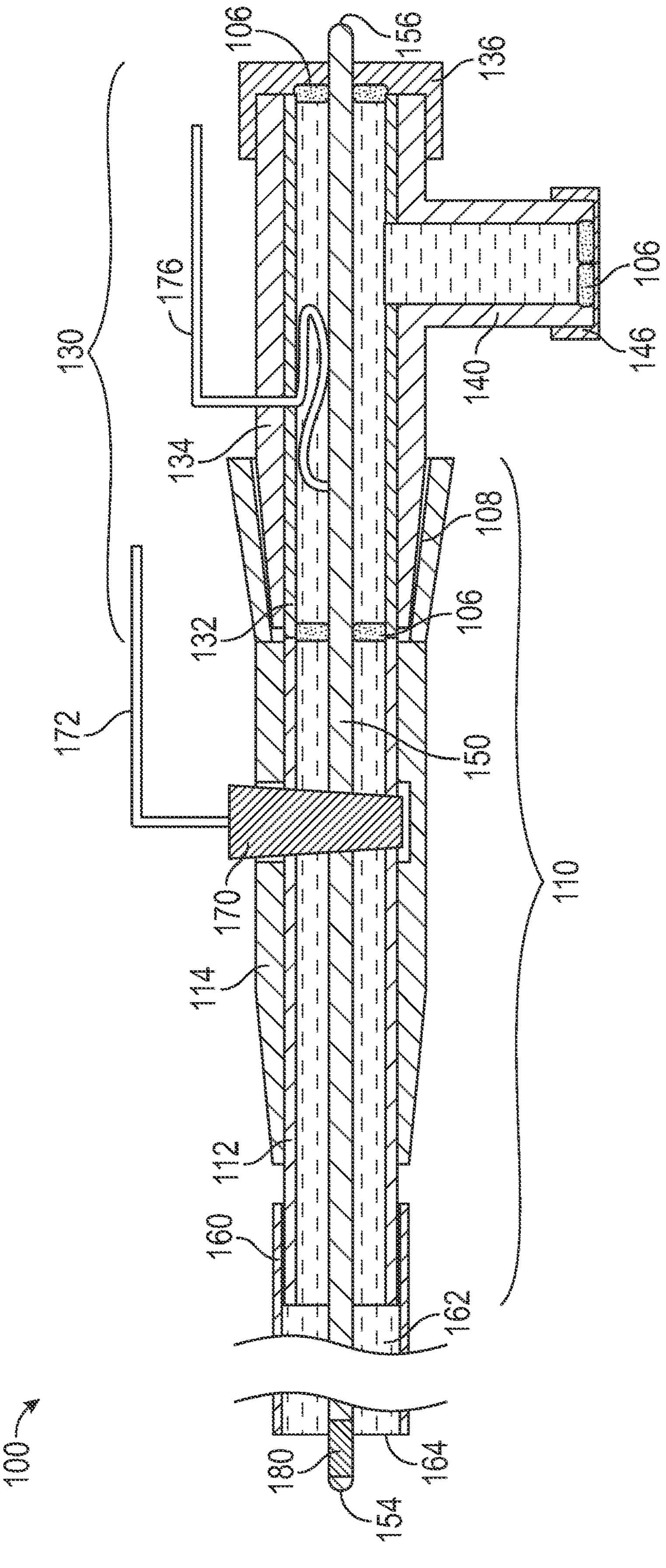
FIG. 2B shows a cross-section view of a multi-function adapter system, in accordance with embodiments disclosed herein.

As shown in FIGS. 2A-2B, in an embodiment, the flushing arm 140 can provide a saline solution into the lumen 102 of the system 100 and into the catheter 160. A proximal end of the flushing arm 140 can include a second locking valve 146 configured to selectively control a fluid flow therethrough. As such, once a saline solution has be flushed through the system lumen 102 and the catheter lumen 162, to a distal end of the catheter 160, the second locking valve 146 can be closed to "lock" the solution flow and establish a saline column extending to a distal end 164 of the catheter 160 (FIG. 2B).

In an embodiment, the catheter adapter housing 114 can include a socket 116 configured to receive a portion of the clip 170 therein. In use, a user can insert the clip 170 into the socket 116 and engage a portion of the first cannula 112 to establish an electrical connection therebetween (FIG. 2B). As such, an electrical pathway can be established between the distal tip of the catheter 160, through the saline column, first cannula 112, clip 170, first tether 172 and the sensor 90 and/or multi-modal tracking system 80. The electrical pathway can communicate an ECG signal received at the distal tip 164 of the catheter 160 to the multi-modal tracking system 80 to determine a position of the distal tip 164 of the catheter 160 relative to a target location.

In an embodiment, as shown in FIG. 2A, the flushing adapter 130 can include a second cannula 132 defining a second portion of the system lumen 102 and also formed of a metallic or conductive material, as described herein. In an embodiment, the second tether 176 can be fixedly coupled with the second metal cannula 132 to provide an electrical connection therebetween. As such, an electrical pathway can be established between the distal tip 164 of the catheter 160, through the saline column, second cannula 132, second tether 176 and to the sensor 90 and/or multi-modal tracking system 80. The electrical pathway can communicate an ECG signal received at the distal tip 164 of the catheter 160 to the multi-modal tracking system 80 to determine a position of the distal tip 164 of the catheter 160 relative to a target location.

In an embodiment, the catheter adapter 110 including the clip 170 and the first tether 172 can establish a first electrical pathway, and the flushing adapter 130 including the second tether 176 can establish a second electrical pathway. Advantageously, the multi-modal tracking system 80 can use both the first electrical pathway and the second electrical pathway to cross-check the ECG signal received, and determine an accuracy of the position of the distal tip 164 of the catheter 160. For example, where a difference between the position calculated by the first pathway and the position calculated by the second pathway is relatively large, the estimated position can be averaged between the two signals and/or an accuracy rating or confidence rating can be categorized as relatively low. Alternatively, where the difference between the two pathways is relatively small, the position can be averaged and/or the accuracy rating can be relatively high. The position and accuracy rating can then be displayed to the user by the multi-modal tracking system 80.

Advantageously, the system 100 including the catheter adapter 110 and the clip 170 can provide a versatile means for establishing an electrical pathway since the clip 170 can be selectively detached from the catheter adapter 110 and coupled directly with one of the stylet 150, guidewire 250, access needle, or catheter 160, as needed depending on the specific catheter placement procedure being used, as described in more detail herein. Further, the flushing adapter 130 including the second tether 176 fixedly coupled thereto can form a reliable electrical connection and can maintain at least one electrical pathway between the catheter distal tip 164 and the multi-modal tracking system 80 while the clip 170 can be exchanged between one of the catheter adapter 110, stylet 150, guidewire 250, access needle, or catheter 160, as needed. Similarly, the clip 170 can maintain at least one electrical pathway between the catheter distal tip 164 and the multi-modal tracking system 80 while one or more of the stylet 150, guidewire 250, or flushing adapter 130 is exchanged, as described in more detail herein. Advantageously, the system 100 including both the catheter adapter 110 and the flushing adapter 130 can provide a fail-safe system to ensure the electrical communication with a distal tip of the catheter 160 remains uninterrupted and the position of the distal tip of the catheter 160 can be continually verified.

In an embodiment, the system 100 can further include one of a stylet 150 or guidewire 250, extending through the system lumen 102, into the catheter lumen 162 and to a distal tip 164 of the catheter 160. In an embodiment, as shown in FIGS. 2A-2B, the stylet 150 can be a separate structure and can be slidably engaged with the system lumen 102. In an embodiment, the stylet 150 can be selectively locked in position relative one of the lumen 102 or the distal tip 164 of the catheter 160 using the locking valve 136, as described herein.

In an embodiment, the stylet 150 or guidewire 250 can be formed of a conductible material to provide an electrical pathway therethrough. In an embodiment, the clip 170 can be disengaged from the catheter adapter 110 and coupled with a proximal end of one of the stylet 150 or the guidewire 250. As such, a third electrical pathway can be established between a distal tip 154 of the stylet 150 disposed adjacent the distal tip 164 of the catheter 160, through the stylet 150, clip 170, first tether 172 and to the sensor 90 and/or multi-modal tracking system 80.

Advantageously, a user can switch the clip 170 between the socket 116 and the stylet 150 depending on reliability of the connection, strength of the electrical signal, the stage in the placement of the catheter 160, or the like, to cross-reference the accuracy of a second electrical pathway, alternate between electrical pathways to ensure a constant signal is provided to the sensor 90, combinations thereof, or the like.

Figure 2C:
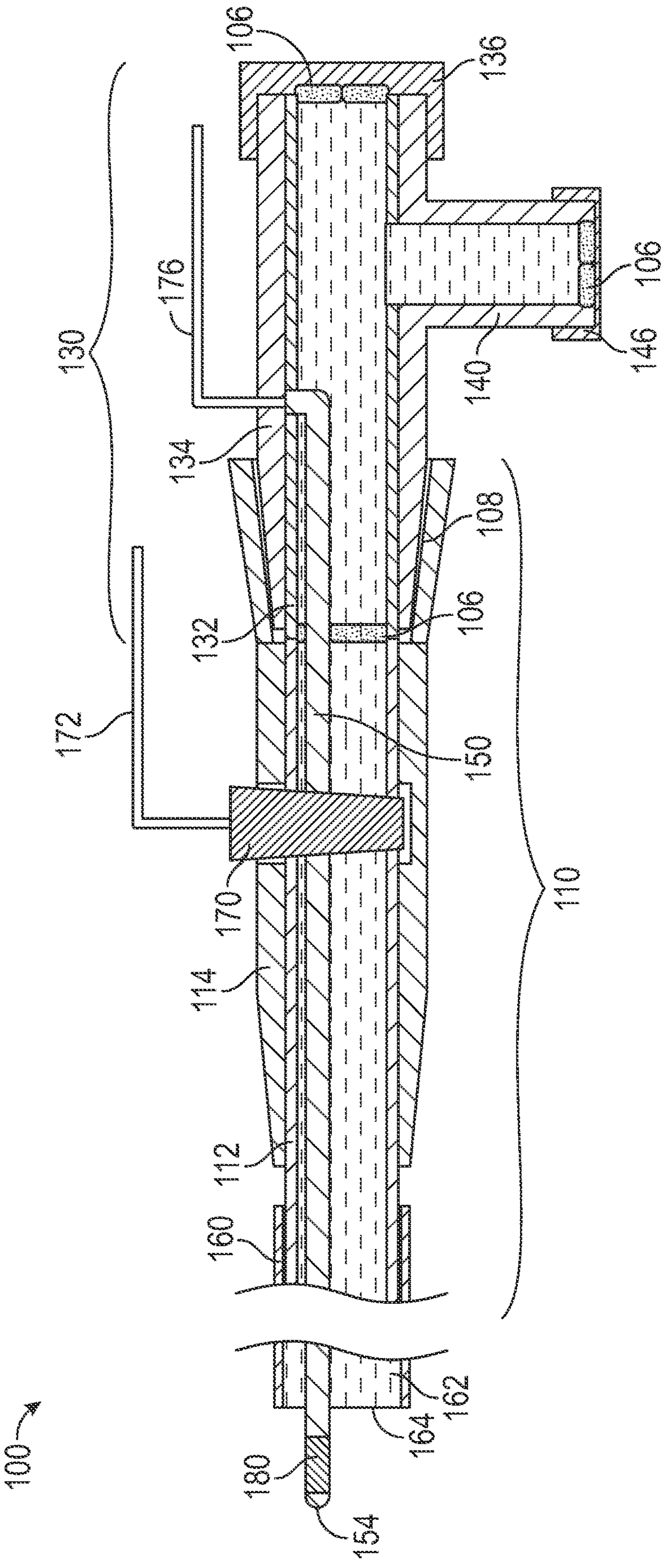
FIG. 2C shows a cross-section view of a multi-function adapter system including a stylet fixedly coupled thereto, in accordance with embodiments disclosed herein.

In an embodiment, as shown in FIGS. 2B-2C, the second tether 176 can be fixedly coupled with the stylet 150 or guidewire 250 to provide an electrical connection therebetween. For example, as shown in FIG. 2B, the second tether 176 can extend through a wall of the flushing adapter housing 134 and be fixedly attached to the stylet 150. In an embodiment, the second tether 176 can be fixedly attached directly to a proximal end 156 of the stylet 150, i.e. without contacting the flushing adapter 130, for example similar to the configuration shown in FIG. 2D. In an embodiment, the second tether 176 can be fixedly attached to the stylet 150 using adhesive, welding, soldering, bonding, or the like, to provide a reliable electrical connection therewith. Advantageously, the stylet 150 can still be slidably engaged with the system lumen 102.

As shown in FIG. 2C, in an embodiment, the stylet 150 can be fixedly coupled with the flushing adapter housing 134 to provide a reliable connection therewith. As such, in an embodiment, a user can remove the stylet 150 from the catheter 160 by detaching the flushing adapter 130 from the catheter adapter housing 110 and withdrawing the flushing adapter 130 proximally. Advantageously, the stylet 150 formed integrally with the flushing adapter housing 130 can provide additional electrical pathways between the distal tip 164 of the catheter 160 through one or both of the stylet 150 and the saline column to the multi-modal tracking system 80. In an embodiment, the stylet 150 can be fixedly coupled with the catheter adapter housing 114 to provide a reliable connection therewith and the second tether 176 can be coupled with the catheter adapter 110 to provide a second electrical pathway, as described herein.

Figure 2D:
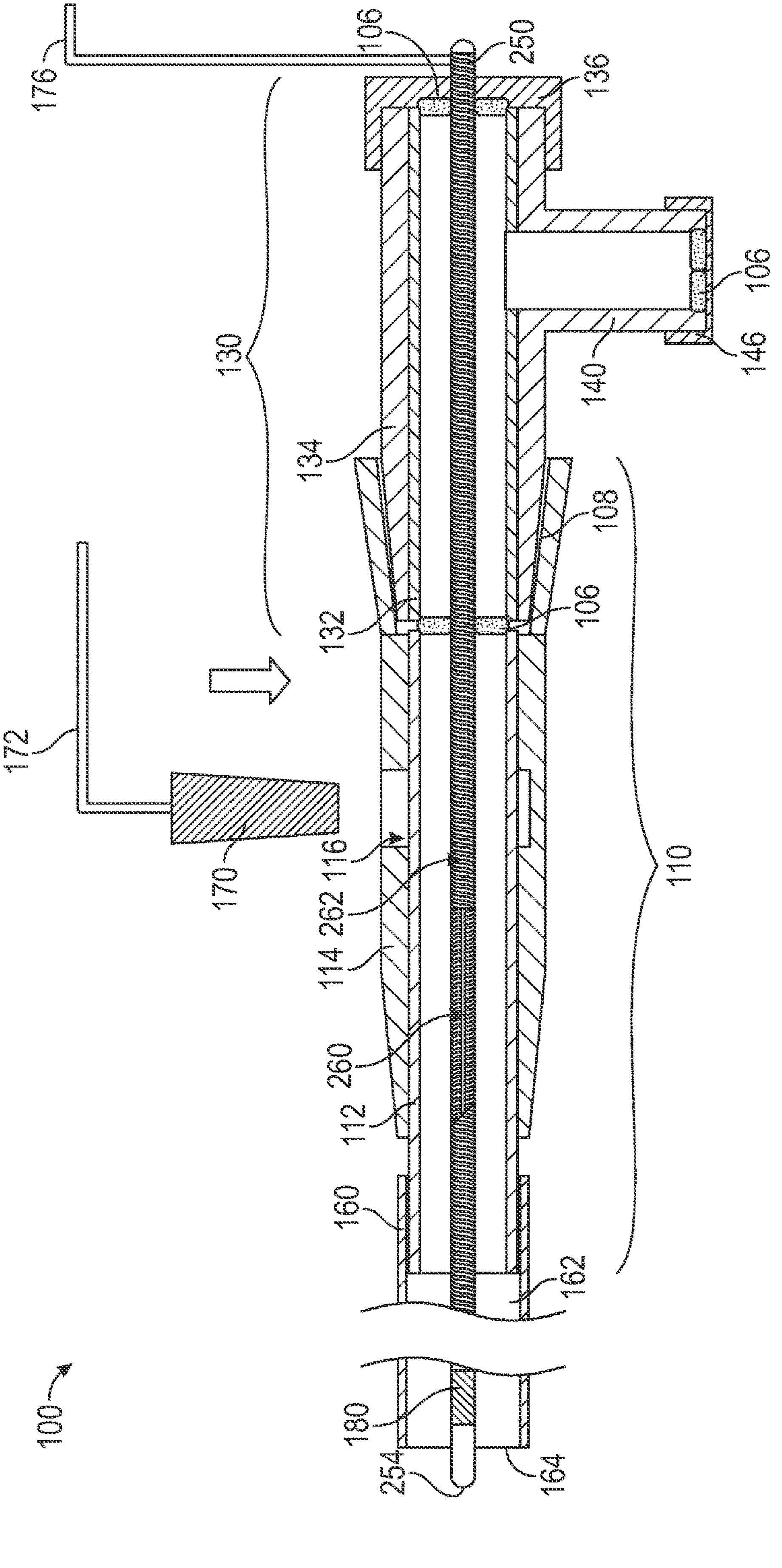
FIG. 2D shows a cross-section view of a multi-function adapter system including a guidewire, in accordance with embodiments disclosed herein.

As shown in FIG. 2D, in an embodiment, the system 100 can further include a guidewire 250 configured to extend through the system lumen 102, through the catheter lumen 162 and into a vasculature of the patient. In an embodiment, the guidewire 250 can be formed of a conductive material and provide an electrical pathway between the distal tip 254 of the guidewire 250, adjacent to the catheter distal tip 164, and one or both of the clip 170 and first tether 172 electrical pathway, or flushing adapter 130 and second tether 176 electrical pathway, or the like, as described herein. In an embodiment, the guidewire 250 can include a core wire 260 and a coil wire 262 extending helically thereover. In an embodiment, one or both of the core wire 260 and the coil wire 262 can provide an electrical pathway as described herein. Further a proximal end of one or both of the core wire 260 or the coil wire 262 can be coupled to one or both of the first tether 172 or the second tether 176, as described herein.

In an embodiment, one or both of the stylet 150 or the guidewire 250 can include a magnetic element 180, coupled therewith adjacent a distal tip 154, 254 thereof. The magnetic element 180 can be a permanent magnet or an electromagnet. Advantageously, the multi-modal tracking system 80 can detect a magnetic field strength and determine a location of the distal tip 164 of the catheter 160 disposed adjacent the magnetic element 180, as the catheter 160 is advance through the vasculature of the patient. Further details and embodiments of multi-modal tracking systems 80 using one or more of ultrasound imaging, magnetic tracking or tip confirmation, ECG tracking or tip confirmation, combinations thereof or the like, can be found in U.S. Pat. Nos. 8,971,994, 9,492,097, 9,636,031, 10,238,418, 10,966,630, 11,027,101, U.S. 2018/0116551, U.S. 2018/0304043, U.S. 2019/0069877, U.S. 2019/0099108, U.S. 2020/0054858, U.S. 2020/0237255, U.S. 2020/0345983, which are herein incorporated by reference in their entirety.

In an exemplary method of use, a multi-function adapter system ("system") 100 is provided, as described herein. A user can couple a first cannula 112 extending from a distal tip of the catheter adapter housing 114 with a proximal end of a catheter 160 in an interference fit engagement, or the like and provide fluid communication therebetween. In an embodiment, a distal end of a flushing adapter 130 can be coupled with a proximal of the catheter adapter 110. In an embodiment, a stylet 150 or guidewire 250 can be fixedly coupled with the flushing adapter 130. As such, coupling the flushing adapter 130 can further include extending the stylet 150 or guidewire 250 through the first cannula 112 and into the catheter lumen 162. When the flushing adapter 130 is engaged with the catheter adapter 110, a distal tip of the stylet 150 or guidewire 250 can align with a distal tip 164 of the catheter 160.

In an embodiment, the stylet 150 or guidewire 250 can be formed as a separate structure from the flushing adapter 130. As such, once the flushing adapter 130 is coupled with the catheter adapter 110, the stylet 150 or the guidewire 250 can be slidably engaged with the system lumen 102. A distal tip of the stylet 150 or the guidewire 250 can extend to a distal tip 164 of the catheter 160. In an embodiment, the position of the stylet 150 or the guidewire 250 can be locked relative to the system lumen 102 using locking valve 136. In an embodiment, a syringe, medical line, or the like can be coupled with a flushing arm 140 of the flushing adapter 130 and can flush the system lumen 102 and the catheter lumen 162 with a saline solution. A second locking valve 146 can then lock the saline solution and establish a saline column.

In an embodiment, one of the stylet 150 or the guidewire 250 can include a magnetic element 180 disposed at a distal tip thereof. The distal tip of the catheter 160 can then be advanced through a vasculature of a patient towards a target location. One or both of the sensor 90 and the multi-modal tracking system 80 can detect a magnetic field strength of the magnetic element 180 to track a location of the distal tip 164 of the catheter 160 as it travels through the vasculature towards the target location. Optionally, the multi-modal tracking system 80 can further include an ultrasound imaging system configured to image a subcutaneous portion of the patient. As the distal tip 164 of the catheter 160 approaches a target location, the system 100 can detect an ECG signal at the distal tip 164 of the catheter 160 to confirm a position thereof relative to the target location with much higher accuracy that can be achieved with the magnetic tracking modality. The system 100 can provide one or more electrical pathways to provide the ECG signal to the multi-modal tracking system 80. ECG signals from two or more electrical pathways can be cross-referenced confirm accuracy of placement, and maintain a consistent ECG signal during the placement procedure.

Once the catheter 160 has been placed successfully, the stylet 150 or guidewire 250 can be withdrawn proximally. Advantageously, the catheter adapter 110 can maintain an ECG electrical pathway to confirm the distal tip of the catheter 160 has not been dislodged during withdrawal of the stylet 150 or guidewire 250. In an embodiment, the flushing adapter 130 can be disconnected from the catheter adapter 110 and can be withdrawn proximally. In an embodiment, one of the stylet 150 or the guidewire 250 can be fixedly coupled to the flushing adapter 130 as described herein. As such, disconnecting and withdrawing the flushing adapter 130 from the catheter adapter 110 can include withdrawing the stylet 150 and guidewire 250 from the catheter lumen 162. Advantageously, the clip 170 and catheter adapter 110 can maintain an ECG electrical pathway to confirm the distal tip 164 of the catheter 160 has not been dislodged during disconnection and withdrawal of the flushing adapter 130 and/or stylet 150 or guidewire 250.

In an embodiment, the catheter adapter 110 can then be detached from the catheter 160 and the stylet 150 can be reinserted into the catheter 160 with the clip 170 coupled thereto. The distal tip stylet 150 can be advanced to the distal tip of the catheter 160 and the multi-modal tracking system 80 can detect an ECG signal at the distal tip of the catheter 160 to reconfirm the distal tip of the catheter 160 has not been dislodged from the target location.

In an embodiment, a port or similar subcutaneous access device can be coupled to the catheter 160 by urging a stem of the port into a proximal end of the catheter lumen 162. During the process of coupling the port to the catheter 160, a distal tip of the catheter 160 can be dislodged. To reconfirm the distal tip of the catheter 160 is correctly placed, an access needle, e.g. a Huber needle or the like, can access the port and catheter 160 assembly and flush the assembly with a saline solution to establish a saline column. The clip 170 of the system 100 can then be coupled with the access needle to establish an electrical pathway with a distal tip of the catheter 160, through the saline column, the access needle, and the clip 170, to reconfirm the position of the distal tip 164 of the catheter 160.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter tip confirmation system, comprising:

a catheter adapter having a housing including a first cannula defining a lumen, the first cannula formed of an electrically conductive material, a distal end of the housing of the catheter adapter configured to engage a proximal end of a catheter and provide fluid communication with the first cannula;

a clip coupled to a first tether and engaged with a socket disposed in the housing of the catheter adapter to releasably engage the first cannula, the clip configured to receive a first ECG signal;

a flushing adapter releasably coupled to a proximal end of the housing of the catheter adapter and configured to provide a saline column within the first cannula and the catheter, the flushing adapter including a second tether fixedly coupled thereto and configured to receive a second ECG signal; and an elongate medical device extending through the lumen of the first cannula, a distal tip of the elongate medical device extending to a distal tip of the catheter, the elongate medical device including a magnet disposed at the distal tip thereof.

2. The catheter tip confirmation system according to claim 1, wherein the second tether is coupled to the elongate medical device to receive the second ECG signal from the distal tip of the elongate medical device.

3. The catheter tip confirmation system according to claim 1, wherein the elongate medical device includes one of a stylet, a guidewire, or a coil-over-core guidewire.

4. The catheter tip confirmation system according to claim 1, wherein the second tether is coupled to a second cannula defining a lumen of the flushing adapter and in fluid communication with the first cannula, the second tether configured to receive the second ECG signal from the saline column extending to the distal tip of the catheter.

5. The catheter tip confirmation system according to claim 1, wherein the clip is configured to be selectively detached from the first cannula and coupled with a proximal portion of the elongate medical device to receive the first ECG signal from the distal tip of the elongate medical device.

6. The catheter tip confirmation system according to claim 1, wherein the elongate medical device is fixedly coupled to the flushing adapter.

7. The catheter tip confirmation system according to claim 1, wherein the flushing adapter further includes a flushing arm configured to provide fluid communication therewith.

8. The catheter tip confirmation system according to claim 1, wherein the flushing adapter further includes a locking valve configured to transition between a locked position and an unlocked position, the locking valve in the locked position configured to inhibit longitudinal movement of the elongate medical device relative to the flushing adapter.

9. The catheter tip confirmation system according to claim 8, wherein the locking valve further includes a valve member configured to control a fluid flow therethrough in both the locked position and the unlocked position.

10. The catheter tip confirmation system according to claim 1, further including a console configured to compare one of the first ECG signal and the second ECG signal to determine an accuracy of a location of the distal tip of the catheter.

11. The catheter tip confirmation system according to claim 10, wherein the console is further configured to detect a magnetic field of the distal tip of the elongate medical device and determine a position of the distal tip of the catheter within a body of a patient.

12. The catheter tip confirmation system according to claim 1, wherein the first cannula is formed of a metal or an alloy.

13. The catheter tip confirmation system according to claim 1, wherein the catheter includes one of a central venous catheter, a peripherally inserted central catheter, a rapidly insertable central catheter, a midline catheter, a single lumen catheter, a multi-lumen catheter, or a dialysis catheter.

14. A method of determining a location of a distal tip of a catheter within a body of a patient, comprising:

coupling a multi-functional adapter system to a proximal end of the catheter, the multi-functional adapter system comprising:

a catheter adapter including a first cannula formed of a conductive material and in fluid communication with the catheter;

a flushing adapter coupled to a proximal end of the catheter adapter; and a clip coupled to a first tether;

establishing a saline column within the first cannula and the catheter;

extending an elongate medical device through the first cannula and into a lumen of the catheter;

receiving a first ECG signal by one of the saline column or the elongate medical device;

receiving a second ECG signal by one of the saline column or the elongate medical device and different from the first ECG signal; and determining the location of the distal tip of the catheter using one or both of the first ECG signal and the second ECG signal.

15. The method according to claim 14, further including comparing the first ECG signal with the second ECG signal to determine an accuracy of the location of the distal tip of the catheter.

16. The method according to claim 14, further including engaging the clip with a slot disposed in a housing of the catheter adapter to contact the first cannula and receive the first ECG signal.

17. The method according to claim 14, further including engaging the clip with the elongate medical device to receive the first ECG signal.

18. The method according to claim 14, wherein the flushing adapter includes a second cannula in fluid communication with the first cannula, and a second tether fixedly coupled thereto and configured to receive the second ECG signal.

19. The method according to claim 14, wherein the flushing adapter includes a second tether fixedly coupled to the elongate medical device and configured to receive the second ECG signal.

20. The method according to claim 14, further including detecting a magnetic field strength of a magnet disposed at a distal tip of the elongate medical device to track the location of the distal tip of the catheter within the body of the patient.

21. The method according to claim 14, wherein the elongate medical device includes one of a stylet, a guidewire, or a coil-over-core guidewire.

22. The method according to claim 14, further including disengaging the catheter adapter from the catheter, coupling a subcutaneous access device to the catheter, accessing the subcutaneous access device with an access needle and coupling the clip with the access needle to receive the first ECG signal.

23. The method according to claim 14, wherein the catheter includes one of a central venous catheter, a peripherally inserted central catheter, a rapidly insertable central catheter, a midline catheter, a single lumen catheter, a multi-lumen catheter, or a dialysis catheter.

* * * * *